(12) United States Patent
Small et al.

(10) Patent No.: US 8,628,652 B2
(45) Date of Patent: *Jan. 14, 2014

(54) ELECTROCHEMICALLY DRIVEN PUMP

(75) Inventors: Hamish Small, Leland, MI (US); Yan Liu, Palo Alto, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/364,078

(22) Filed: Feb. 1, 2012

(65) Prior Publication Data

US 2012/0138474 A1 Jun. 7, 2012

Related U.S. Application Data (62) Division of application No. 12/192,781, filed on Aug. 15, 2008, now Pat. No. 8,133,373.

(51) Int. Cl.
*B01D 61/44* (2006.01)

(52) U.S. Cl.
USPC ............ 204/522; 204/523; 204/633; 204/634

(58) Field of Classification Search
USPC .......................... 204/522, 523, 542, 633, 634
See application file for complete search history.

(56) References Cited

U.S. PATENT DOCUMENTS

| | | | |
|---|---|---|---|
| 4,357,217 A | 11/1982 | Kuehn et al. | |
| 4,532,811 A | 8/1985 | Miller, Jr. et al. | |
| 5,352,360 A | 10/1994 | Stillian et al. | |
| 6,436,719 B1 | 8/2002 | Srinivasan et al. | |
| 6,610,546 B1 | 8/2003 | Liu et al. | |
| 6,613,235 B1 * | 9/2003 | Anderson et al. | 210/670 |
| 6,813,944 B2 | 11/2004 | Mayer et al. | |
| 8,133,373 B2 * | 3/2012 | Small et al. | 204/522 |
| 2006/0057733 A1 | 3/2006 | Liu et al. | |

FOREIGN PATENT DOCUMENTS

| | | |
|---|---|---|
| WO | WO 98/32525 A1 | 7/1998 |
| WO | WO 00/44477 A1 | 8/2000 |
| WO | WO 02/095341 A1 | 11/2002 |
| WO | WO 03/078331 A2 | 9/2003 |
| WO | WO 2004/024302 A1 | 3/2004 |
| WO | WO 2006/113306 A2 | 10/2006 |
| WO | WO 2006/128039 A2 | 11/2006 |
| WO | WO 2007/011919 A2 | 1/2007 |
| WO | WO 2009/064797 A2 | 5/2009 |
| WO | WO 2009/108545 A1 | 9/2009 |

* cited by examiner

*Primary Examiner* — Arun S Phasge
(74) *Attorney, Agent, or Firm* — Dave Brezner (57) ABSTRACT

A continuous electrochemical pump comprising a water generator compartment, an anode compartment on one side of said generator compartment, a cation exchange barrier, separating the generator compartment from the anode compartment, it first electrode in electrical communication with the anode compartment, a cathode compartment adjacent the generator chamber, an anion exchange barrier, separating the generation compartment from the cathode compartment, and a second electrode in electrical communication with the cathode compartment. Use of the pump as a sample concentrator. A feedback loop for the pump. A reservoir, with or without an intermediate piston, on the output side of the pump.

4 Claims, 8 Drawing Sheets

Figure 8

ELECTROCHEMICALLY DRIVEN PUMP

CROSS-REFERENCE TO RELATED APPLICATION

This application is a divisional of U.S. application Ser. No. 12/192,781 filed on Aug. 15, 2008.

BACKGROUND OF THE INVENTION

A variety of liquid pumps are used to drive liquid samples in analytical systems. For example, for liquid chromatography (LC), a pump is used to drive liquid eluent through a stationary separation medium phase, such as a chromatography column packed with ion-exchange resin, and through connected devices that modify and/or monitor the effluent from the stationary phase. Such pumps preferably produce steady flow which is easily and precisely controllable. Also, separation media in the form of packed beds of small particles or beads can create high resistance to liquid flow. Thus, the pump should be capable of pumping against high back pressures, e.g., 1000 psi or more. A typical liquid chromatography pump is of the mechanical, dual-piston type that incorporates components such as pistons, seals, check valves, and the like. To meet and maintain the stringent requirements of long term use, e.g. use for tens of thousands of cycles, the moving and stationary components must be extremely durable. Thus, the pump design and material of construction and fabrication can be the most costly component in an LC system.

In the past, flow rates in LC have typically been about 1-2 ml/min. Newer methods employ separation columns of very small internal diameter (e.g., 100 to 400 µm) and operate the separation processes at very low flow rates (e.g., <10 µL/min). There is a need for a pump which can operate at such low flow rates which is (a) stable, and easily and precisely controllable, (b) capable of maintaining flow against high back pressures and (c) less expensive to build and more durable than conventional LC pumps.

SUMMARY OF THE INVENTION

A continuous electrochemical pump is provided comprising a water generator compartment having an outlet; an anode compartment disposed adjacent one side of the generator compartment; a cation exchange barrier, with exchangeable ions predominantly in the hydronium ion form, separating said generator compartment from said anode compartment, the cation exchange barrier being capable of passing cations but not anions and of blocking bulk liquid flow; a first electrode in electrical communication with the anode compartment; a cathode compartment disposed adjacent the generator chamber; an anion exchange barrier, with exchangeable ions predominantly in the hydroxide ion form, separating the generation compartment from the cathode compartment, the anion exchange barrier being capable of passing anions but not cations and of blocking bulk liquid flow; and a second electrode in electrical communication with the cathode compartment.

A method is provided for generating water using an electrochemical pump comprising an aqueous liquid generator compartment, and having an outlet; an anode compartment containing water and disposed adjacent to said generator compartment; a cation exchange barrier separating the generator compartment from the anode compartment; the cation exchange barrier being capable of passing cations but not anions and of blocking bulk liquid flow; a first electrode in electrical communication with the anode compartment; a cathode compartment containing water and adjacent to the generator chamber; an anion exchange barrier separating the generator compartment from the cathode compartment; the anion exchange barrier being capable of passing anions but not cations and of blocking bulk liquid flow; and a second electrode in electrical communication with the cathode compartment, the method comprising passing an electric current between the first and second electrodes through the water in the anode and cathode compartments, and through the cation and anion exchange barriers, to generate hydroxide ions in the cathode compartment and hydronium ions in the anode compartment; passing the generated hydroxide ions through the anion exchange barrier and the generated hydronium ions through the cation exchange barrier into the generator compartment to electrochemically generate water; and flowing the generated water in a stream out of the generation compartment.

A continuous electrochemical concentrator in an analytical system is provided comprising a water generator compartment having an outlet; an anode compartment disposed adjacent one side of the generator compartment; a cation exchange barrier separating the generator compartment from the anode compartment, the cation exchange barrier being capable of passing cations but not anions and of blocking bulk liquid flow; a first electrode in electrical communication with the anode compartment; a cathode compartment disposed adjacent the generator chamber; an anion exchange barrier separating the generation compartment from the cathode compartment, the anion exchange barrier being capable of passing anions but not cations and of blocking bulk liquid flow; a second electrode in electrical communication with the cathode compartment; and a detector in fluid communication with the water generator compartment outlet in the absence of a sample injector for the supply of sample, other than sample supplied from said water generator compartment outlet, disposed between the generator compartment outlet and the detector.

A method is provided for concentrating and detecting analyte anions and cations in a water sample using a concentrator comprising an aqueous liquid generator compartment having an outlet; an anode compartment containing a first portion of the analyte anion- and cation-containing water sample and disposed adjacent to the generator compartment; a cation exchange barrier separating the generator compartment from the anode compartment; the cation exchange barrier being capable of passing cations but not anions and of blocking bulk liquid flow, a first electrode in electrical communication with the anode compartment; a cathode compartment containing a second portion of the analyte anion- and cation-containing water sample and adjacent to the generator chamber; an anion exchange barrier separating the generator compartment from the cathode compartment; the anion exchange, barrier being capable of passing anions but not cations and of blocking bulk liquid flow, and a second electrode in electrical communication with the cathode compartment, the method comprising passing an electric current between the first and second electrodes through the first and second water sample portions in the anode and cathode compartments, and through the cation and anion exchange membranes, to generate hydroxide ions in the cathode compartment and hydronium ions in the anode compartment; passing the generated hydroxide ions and analyte anions in the water sample through the anion exchange barrier and the generated hydronium ions and analyte cation in the water sample through the cation exchange barrier into the generator compartment to electrochemically generate a water product sample including the passed analyte cations and anions; and flowing the generated water product sample in a stream out of the generator compartment to a detector to detect the analyte cations and anions in the water product sample in the absence of the injection of any additional sample between the generator compartment and the detector.

A continuous electrochemical pump system is provided comprising a water generator compartment having an outlet; an anode compartment disposed adjacent one side of the generator compartment; a cation exchange barrier separating the generator compartment from the anode compartment, the cation exchange barrier being capable of passing cations but not anions and of blocking bulk liquid flow; a first electrode in electrical communication with the anode compartment; a cathode compartment disposed adjacent the generator chamber, an anion exchange barrier separating the generation compartment from the cathode compartment, the anion exchange barrier being capable of passing anions but not cations and of blocking bulk liquid flow; a second electrode in electrical communication with the cathode compartment; an outlet conduit in fluid communication with the water generator compartment; and a flow controller in fluid communication with the outlet conduit.

A method is provided for generating water using an electrochemical pump comprising an aqueous liquid generator compartment, and having an outlet; an anode compartment containing water and disposed adjacent to the generator compartment; a cation exchange barrier separating the generator compartment from the anode compartment; the cation exchange barrier being capable of passing cations but not anions and of blocking bulk liquid flow, a first electrode in electrical communication with the anode compartment; a cathode compartment containing water and adjacent to the generator chamber; an anion exchange barrier separating the generator compartment from the cathode compartment; the anion exchange barrier being capable of passing anions but not cations and of blocking bulk liquid flow, and a second electrode in electrical communication with the cathode compartment, said method comprising passing an electric current between the first and second electrodes through the water in the anode and cathode compartments, and through the cation and anion exchange barriers, to generate hydroxide ions in the cathode compartment and hydronium ions in the anode compartment; passing the generated hydroxide ions through the anion exchange barrier and the generated hydronium ions through the cation exchange barrier into the generator compartment to electrochemically generate water in a stream, flowing the generated water stream out of the generation outlet; and determining the flow rate of the generated water downstream from the generator compartment.

A continuous electrochemical pump is provided comprising a water generator compartment having an outlet; an anode compartment disposed adjacent one side of the generator compartment; a cation exchange barrier separating the generator compartment from the anode compartment, the cation exchange barrier being capable of passing cations but not anions and of blocking bulk liquid flow; a first electrode in electrical communication with anode compartment; a cathode compartment disposed adjacent the generator chamber; an anion exchange barrier separating the generation compartment from the cathode compartment, the anion exchange barrier being capable of passing anions but not cations and of blocking bulk liquid flow; a second electrode in electrical communication with the cathode compartment; and a piston disposed between the water generator compartment and its outlet capable of separating water produced in the generator compartment from the opposite side of the piston and capable of transmitting pressure applied to the piston by the generated water.

A method is provided for generating water using an electrochemical pump comprising an aqueous liquid generator compartment comprising a piston, other liquid on the opposite side of the liquid piston from the generator compartment, an anode compartment containing water and disposed adjacent to the generator compartment; a cation exchange barrier separating the generator compartment from the anode compartment; the cation exchange barrier being capable of passing cations but not anions and of blocking bulk liquid flow, a first electrode in electrical communication with the anode compartment; a cathode compartment containing water and adjacent to the generator chamber; an anion exchange barrier separating the generator compartment from the cathode compartment; the anion exchange barrier being capable of passing anions but not cations and of blocking bulk liquid flow, and a second electrode in electrical communication with the cathode compartment, the method comprising passing an electric current between the first and second electrodes through the water in the anode and cathode compartments, and through the cation and anion exchange membranes, to generate hydroxide ions in the cathode compartment and hydronium ions in the anode compartment, and passing the generated hydroxide ions through the anion exchange barrier and the generated hydronium ions through the cation exchange barrier into the generator compartment to electrochemically generate water therein to apply pressure to one side of the piston to cause the flow of liquid on the other side of the piston.

A continuous electrochemical pump is provided comprising (a) a water generator compartment having an outlet, (b) an anode compartment disposed adjacent one side of the generator compartment, (c) a cation exchange barrier separating the generator compartment from the anode compartment, the cation exchange hairier being capable of passing cations but not anions and of blocking bulk liquid flow, (d) a first electrode in electrical communication with the anode compartment, (e) a cathode compartment disposed adjacent the generator chamber, (f) an anion exchange barrier separating the generation compartment from the cathode compartment, the anion exchange barrier being capable of passing anions but not cations and of blocking bulk liquid flow, (g) a second electrode in electrical communication with the cathode compartment, and (h) a fluid reservoir container in fluid communication with the water generator compartment outlet and downstream therefrom.

A method is provided for generating water using an electrochemical pump comprising an aqueous liquid generator compartment, an anode compartment containing water and disposed adjacent to the generator compartment; a cation exchange barrier separating the generator compartment from the anode compartment; the cation exchange barrier being capable of passing cations but not anions and of blocking bulk liquid flow, a first electrode in electrical communication with the anode compartment; a cathode compartment containing water and adjacent to the generator chamber; an anion exchange barrier separating the generator compartment from the cathode compartment; the anion exchange barrier being capable of passing anions but not cations and of blocking hulk liquid flow, and a second electrode in electrical communication with the cathode compartment, and a reservoir of other liquid downstream from the generator compartment outlet; said method comprising (a) passing an electric current between the first and second electrodes through the water in the anode and cathode compartments, and through the cation and anion exchange membranes, to generate hydroxide ions in the cathode compartment and hydronium ions in the anode compartment, and (b) passing the generated hydroxide ions through the anion exchange barrier and the generated hydronium ions through the cation exchange barrier into the generator compartment to electrochemically generate water therein, and flowing the generated water to the other liquid reservoir to displace part of the other liquid in the reservoir.

DETAILED DESCRIPTION OF PREFERRED EMBODIMENTS

This invention relates to an electrochemically driven pump, also termed an electrochemical pump, ("ECP") and particularly one suitable for driving liquid in an LC or other liquid sample analytical systems.

In one embodiment, the ECP includes (a) an aqueous liquid generator compartment having an outlet; (b) an anode compartment adjacent one side of the generator compartment; (c) a cation exchange membrane, with exchangeable ions predominantly in the hydronium-ion form, separating the generator compartment from the anode compartment; (d) a first electrode in electrical communication with the anode compartment; (e) a cathode compartment, disposed adjacent the opposite side of the generator compartment; (f) an anion-exchange membrane, with exchangeable ions predominantly in the hydroxide-ion form, separating the generator compartment from the cathode compartment; and (g) a second electrode in electrical communication with the cathode compartment.

The ECP of the present invention is particularly effective for analytical systems (e.g. LC systems) which use low pumping rates such as 0.001 to 100 µL/min., and, more specifically, about 1-10 µL/min. Such systems use capillary separation columns (e.g., 100 to 400 µm internal diameter) through which the liquid flows. In an LC system, such stationary phases can include chromatography separation medium disposed in a capillary cross-section column, e.g., as disclosed in US Publication 2006-0057733. Suitably, the chromatography medium packing is a packed bed of ion-exchange resin or a flow-through porous monolithic chromatography medium.

Figure 1:
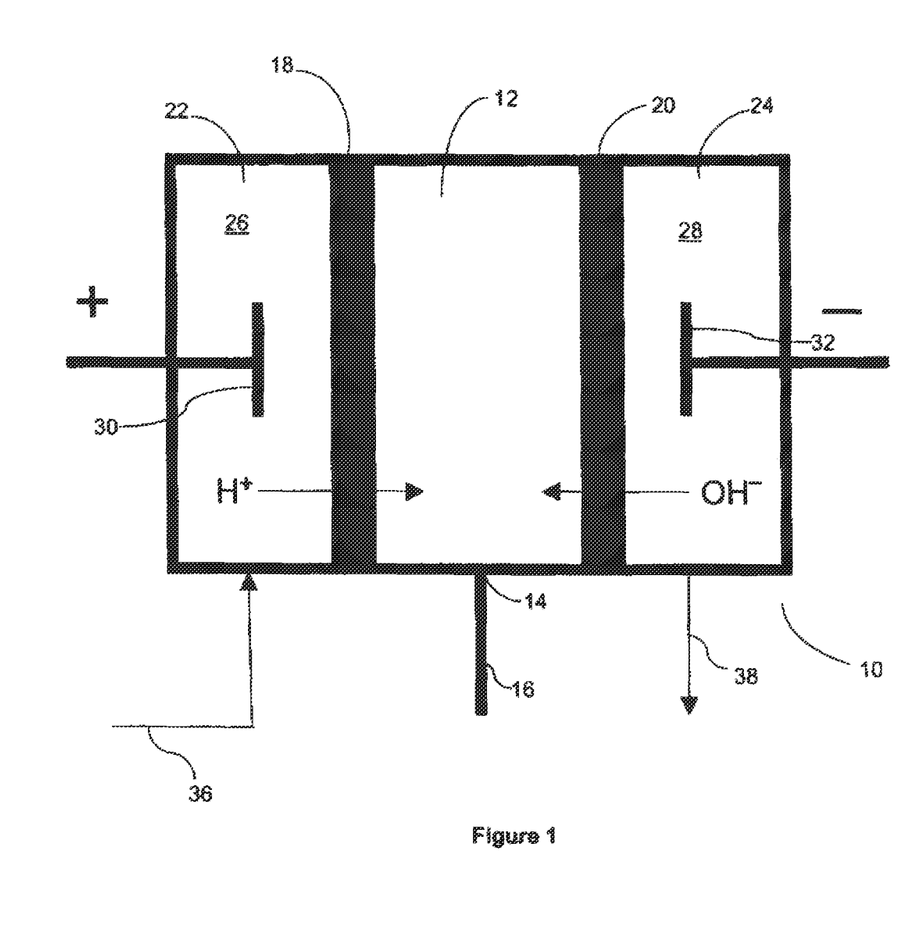
FIGS. 1, 2, 3A and 3B, and 4 are schematic representations of apparatus according to the invention.

A schematic representation of one embodiment of the ECP is illustrated in FIG. 1. The ECP includes a housing 10, having non-conductive walls of any suitable cross-section including cylindrical or rectangular. Within housing 10 is a water generator compartment 12 having a port or outlet 14 connected to an outlet conduit 16. One side of compartment 12 is defined by ion-exchange membrane 18 and the other side by a spaced, generally parallel ion-exchange membrane 20, having exchangeable ions of opposite charge to membrane 18. Membranes 18 and 20 are one form of suitable charged barrier components which pass ions of one charge, positive or negative, but which block bulk liquid flow. Flanking the outside of membranes 18 and 20 are compartments 22 and 24, which serve to contain water source reservoirs 26 and 28 to be used as the sources of water for the ECP. Electrodes 30 and 32 are in electrical communication with membranes 18 and 20, respectively, preferably disposed adjacent or within compartments 22 and 24, respectively. Electrodes 30 and 32 are polarized by attachment to a D.C. power supply (not shown). As illustrated, electrode 30 in compartment 22 is an anode and electrode 32 in compartment 24 is a cathode. In this configuration, the ion-exchange membrane 18 closest to positively charged electrode 30 is a cation-exchange membrane predominantly in the hydronium-ion form. Similarly, when electrode 32 is a cathode, membrane 20 is an anion-exchange membrane predominantly in the hydroxide-ion form.

As illustrated, a stream of water flows in line 36 into compartment 22 and is routed by suitable internal tubing (not shown) through compartment 26 to exit in line 38. Flow can be in the reverse direction or independent sources of water can be employed for each reservoir. Further, in certain systems, the water reservoirs in compartments 22 and 24 may be substantially non-flowing reservoirs with periodic replenishment as needed. In such systems, external cooling, e.g. from a heat exchanger, may be used to dissipate oxygen and hydrogen gas bubbles formed in the water reservoirs, and/or vents may be provided to remove such formed gas bubbles.

Assuming that electrodes 30 and 32 are spaced from membranes 18 and 20, as illustrated, it is preferable to include a charged bridging structure which creates an ion-exchange path between the electrodes and the membranes to facilitate the movement of ions within the device between the electrodes and membranes to thereby reduce electrical resistance. Suitable structure for bridging the gaps between the electrodes and membranes include ion-exchange screens, ion-exchange resin beds, or flow-through ion-exchange monoliths. It is preferable to provide sufficient porosity in these ion-exchange structures so that the water of reservoirs 26 and 28 can contact membranes 18 and 20. The bridging structure in the illustrated compartment 22, also termed an anode component herein, is a cation-exchange material predominantly in the hydronium-ion form, while the bridging structure in compartment 24, also termed the cathode compartment, is an anion-exchange material predominantly in the hydroxide form. For simplicity of description, these ion-exchange bridging structures are not illustrated in FIG. 1.

In an alternative embodiment, the electrodes can be in direct contact with their adjacent membranes. In this embodiment, the charged bridging structures may be eliminated and the electrodes preferably are sufficiently porous so that water in reservoirs 26 and 28 can flow through the electrodes to contact the membranes.

It is preferable, but optional, to include ion-conductive bridging structure in water generator compartment 12 to facilitate movement of ions for a similar reason to that of the charged bridging structure between the electrodes and adjacent membranes. For simplicity of description, this disclosure will refer to cation-exchange material in compartment 12. The bridging structure in generator compartment 12 may either be a cation- or an anion-exchange material predominantly in the hydronium or hydroxide forms, respectively, in a similar physical structure to that in compartments 22 and 24. Alternatively, the bridging structure in generator compartment 12 may also be formed of two layers of ion-exchange material, one cation-exchange material and the other anion-exchange material. In this embodiment, each layer of bridging material would lie adjacent to the membrane of like charge. Thus, the anion-exchange material will be adjacent the anion-exchange membrane and the cation-exchange material will be adjacent to the cation-exchange membrane. In yet another alternative embodiment, a mixture of anion- and cation-exchange materials, e.g., anion- and cation-exchange beads in a packed bed in the hydroxide and hydronium form, also can be used for the ion bridging structure in generator compartment 12. For simplicity of description, the bridging structure in generator compartment 12 is not illustrated in FIG. 1.

The physical structure of the elements in embodiment of FIG. 1 is similar to the structure of the sandwich membrane suppressor illustrated in FIGS. 1-4 of U.S. Pat. No. 5,352,360 (the '360 patent), incorporated herein by reference. In the membrane suppressor, the external compartments are regenerant compartments which serve to remove eluent ions through the membrane from the eluent flowing through the central channel. In contrast, the ECP of the present invention generates water in the central channel by electrochemical reactions at the anode and cathode. Also, the structure of the device is similar to that of FIG. 4 of publication WO 2004/024301 A1. That device is an electrolytic eluent generator in which reservoirs external to a central generator compartment are filled with an acid, base, or salt to electrochemically generate acid or base in the central channel. In the suppressor and eluent generator devices as well as the ECP of the present invention, electrolysis is performed at the anode and cathode.

In the (positively charged) anode compartment 22, in the vicinity of anode 26, the following reaction takes place to generate hydronium ions which pass through membrane 18:

$$6H_2O \rightarrow 4H_3O^+ + O_2 + 4e^- \quad (1)$$

In the (negatively charged) cathode compartment 24 in the vicinity of cathode 32, the following reaction takes place to generate hydroxide ions to pass through membrane 20:

$$4e^- + 4H_2O \rightarrow 4OH^- + 2H_2 \quad (2)$$

In the central water-generation compartment 12, water is generated according to the following equation:

$$OH^- + H_3O^+ \rightarrow 2H_2O \quad (3)$$

When the ECP of FIG. 1 is polarized by application of current across the electrodes, hydronium ions generated at anode 30 pass through the ion-transport bridging structure (if present) and through cation-exchange membrane 18 into water-generator compartment 12. At the same time, an equivalent number of hydroxide ions produced at cathode 32 passes through ion-transport bridging structure, if present, and anion-exchange membrane 20 into water-generator compartment 12 where they unite with the hydronium ions to form water as set forth in Equation (3).

Based on well-known principles of electrolysis, an accumulated current equivalent to 96,500 coulombs (one faraday) will produce one mole (18 grams) of water in compartment 12. As used herein, the water transferred into generator compartment 12 is termed faradaic water. Both the hydronium ion and hydroxide ions have strongly associated water of hydration. That is why the hydrogen ion in water is referred to herein as the $H_3O^+$ (hydronium ion). This strongly attached water of hydration is also transferred into compartment 12. Furthermore, it is believed that the ions moving through the membrane will "drag" a substantial amount of water with them into compartment 12. This is referred to herein as electroosmotically transported water. Assuming compartment 12 has relatively stable dimensions (i.e. it does not significantly expand or contract), then these three sources of water produce water flow through single outlet conduit 16. In this manner, the ECP is capable of supplying water to an LC system or the like, particularly one of capillary dimension, at a rate precisely controlled by the current passing between the ECP anode and cathode.

The water generated in compartment 12 suitably is used in an LC system, such as an ion chromatography system as described in the '360 patent, incorporated by reference. In that regard, the reservoirs 26 and 28 preferably deliver high-purity water, i.e., substantially deionized water. In the embodiment of FIG. 1, the reservoirs may include trace ionic contaminants, e.g., less than about 0.01 ppm, so long as the contaminants do not significantly interfere with chromatographic detection of sample ions.

Since the preferred ECP embodiment generates substantially pure water, a cation-exchange membrane includes exchangeable ions predominantly in the hydronium-ion form while the anion-exchange membrane includes exchangeable ions predominantly in the hydroxide-ion form. As used herein, the term "predominantly in the hydronium-ion form" means that at least 51% and preferably at least 90 to 99 to 99.9% or more of the exchangeable ions are in the hydronium-ion form. Similarly, the term "predominantly in the hydroxide-ion form" means that the exchangeable ions in the anion-exchange membrane are at least 51% and preferably at least 90 to 99 to 99.9% or more in the hydroxide-ion form.

As set forth above, the ECP may be used as a pump in an LC or other analytical system. One specific LC system, a suppressed ion chromatography (IC) system, is illustrated in the '360 patent. The ECP can be substituted for pump 15 illustrated in FIG. 1 of that patent. Like this IC system, the outlet of the generator compartment 12 herein is upstream of a liquid sample injector and in fluid communication therewith. Further, like the IC system of the '360 patent, the present system includes a chromatography separator in the form of a chromatography column downstream from the sample injector, a suppressor downstream from the chromatography column to suppress the eluent, and a sample detector (e.g. a conductivity detector) downstream from the suppressor. In this system, the detector is in fluid communication with the sample injector downstream therefrom, with an intermediate chromatography column and, optionally, a suppressor downstream from it. In a preferred embodiment, the ECP replaces the pump disposed upstream of the sample injector to provide water eluent for carrying the sample to the chromatography column. Preferably, the ECP is the only pump upstream of the sample injector, i.e., excluding any pump used to supply water to compartments 22 and 24.

As set forth above, typical water sources, even de-ionized water, cart include contaminants, and so the ECP pump may not generate pure water. In that regard, the water flowing in conduit 16 out of compartment 12 may have a conductance on the order of several hundred microsiemens or more. Also, the membranes may not he completely in their hydronium-ion and hydroxide-ion forms so that contaminating cations and anions may be chemically driven into the liquid in compartment 12, thus raising its conductance. To avoid interference in chromatography detection for such ionic contaminant in the ECP product stream, a small polishing de-ionizing device such as a de-ionizing column may be disposed downstream from the outlet of the ECP. If the membranes and reservoirs are prepared in relatively pure form, then the load on such a polishing de-ionizing device is relatively low so the device can last a long time before replacement.

Another way to avoid chromatography interference from ionic contamination is to use an ECP to generate water which displaces another fluid from a reservoir downstream from the generator compartment. Fluid displacement systems are disclosed in U.S. Pat. No. 6,436,719, incorporated by reference. In one embodiment, a piston is disposed on the outlet side of the ECP adjacent to a reservoir of a different solution from that generated in the generator compartment. Suitable displaced different solutions include de-ionized water or an acid, base or salt eluent or organic solvents or mixtures of organic solvents and aqueous solutions. The displaced solution can be pumped to the analytical system. The term "piston" encompasses a conventional piston, a flexible bladder, membrane, or the like, or other member that is capable of transferring pressure from the liquid generated in the ECP to such a reservoir on the outlet side of the generator compartment, e.g. for flow to an analytical system. If high-quality water is to be displaced and pumped, then the reservoir is charged with high-purity water. The water output of the ECP generator compartment then applies pressure to the piston to force out the liquid content of the reservoir at a rate controlled by controlling the flow rate of liquid to the other side of the piston in the ECP. Before the ECP expels all of the contents of the reservoir, the reservoir may be recharged to switch to another reservoir charged with pure water. Since the reservoir can contain any fluid, the ECP can have applications other than pumping of water. In principle, it can provide a means of controlled flow of any fluid under atmospheric or pressurized conditions.

In other embodiments of displacement systems, also disclosed in U.S. Pat. No. 6,436,719, no piston is disposed between the generator compartment and the reservoir of the other liquid. Thus, the generated water is in direct contact with the liquid to be displaced. In one embodiment, water generated in the generator compartment flows to the reservoir of liquid through a reservoir inlet at a higher elevation than the reservoir outlet so that the fluid in the reservoir, not the generated water, flows out of the reservoir.

The system of the present invention preferably is dimensioned to be capable of pumping water to a capillary LC system, particularly a capillary ion chromatography system. In that regard, for a device of the type illustrate in FIG. 1 in which the membranes are sheets, suitable dimensions are as follows: compartments 22 and 24 for reservoirs 26 and 28, respectively and include that 1 to 2000 microliters, preferably 5 to 500, and more preferably 20 to 200 µL. Similarly, water generation compartment 12 suitably a volume of 0.1 to 1000 µL and preferably 10 to 100 µL. Membranes 18 and 20 may be of the type illustrated in the '360 patent as well as the ion-exchange screens illustrated therein, except for the substantially reduced dimension of the device compared to a suppressor of the '360 patent.

Conduit 16 is suitably of capillary dimension, e.g., 10 to 500 µm ID. It is noted that, in comparison to sandwich membrane suppressors, the only source of water to water generator compartment 12 is the water generated by the ECP after ionic and molecule flow through membranes 18 and 20. Thus, during operation there is no separate source of flowing liquid into compartment 12, and the only open port for liquid flow is outlet 14 to conduit 16. Another port could be included in compartment 12 such as for filling of the compartment or converting bridging structure in it to appropriate form.

An ECP of the foregoing dimensions could be used to supply a chromatography column or chromatography medium in another type of housing with a volume is about 0.01 to 1000 µL, preferably 1 to 50 µL.

Sufficient current should be applied between the electrodes for the amount of electrolysis which provides the desired flow rate. For a typical capillary LC operation, a typical flow rate is at least 0.01 µL/min. to 10 µL/min or a higher flow rate of 50 µL/min. To minimize the current, it is preferable that the flow rate be less than 5 µL/min. Assuming a flow rate of 1 µL/min, a current in the range of 16-89 milliamps may be sufficient.

A specific embodiment of an ECP ("Pump 1") according to the invention uses a structure similar to that illustrated as the suppressor in FIGS. 1-4 for a suppressed IC system of the '360 patent with some differences. The ECP would replace pump 17 of FIG. 1 in that patent. Referring to FIG. 3 of the '360 patent, the flow channel in gasket 30, containing charged screen 32, corresponds to generation compartment 12 of FIG. 1 herein; the flow channels in gaskets 38 and 40, containing charged screens 41 and 43, respectively, correspond to compartments 22 and 24, respectively, of FIG. 1 herein; ion-exchange membranes 34 and 36 correspond to membranes 18 and 20, respectively; and electrodes 42 and 44 correspond to electrodes 30 and 32, respectively, of FIG. 1 herein. In the pump 1 embodiment, (a) a bridging structure in the form of a screen (not shown in FIG. 1 herein) in the anode compartment 22 between electrode 30 and membrane 18 is a cation exchange screen; (b) membrane 18 is a cation-exchange membrane; (c) a cation exchange screen (not shown in FIG. 1) is placed in the central generation compartment 12; (d) membrane 20 is an anion-exchange membrane (replacing the cation-exchange membrane adjacent the cathode of FIG. 1 in the '360 patent); and (e) a bridging structure in the form of a screen (not shown in FIG. 1) in the cathode compartment 28 between electrode 32 and membrane 20 is an anion-exchange screen. The dimensions of this ECP may be described herein. Only a single outlet port 16 for compartment 12 is open during operation with no inlet ports.

Figure 2:
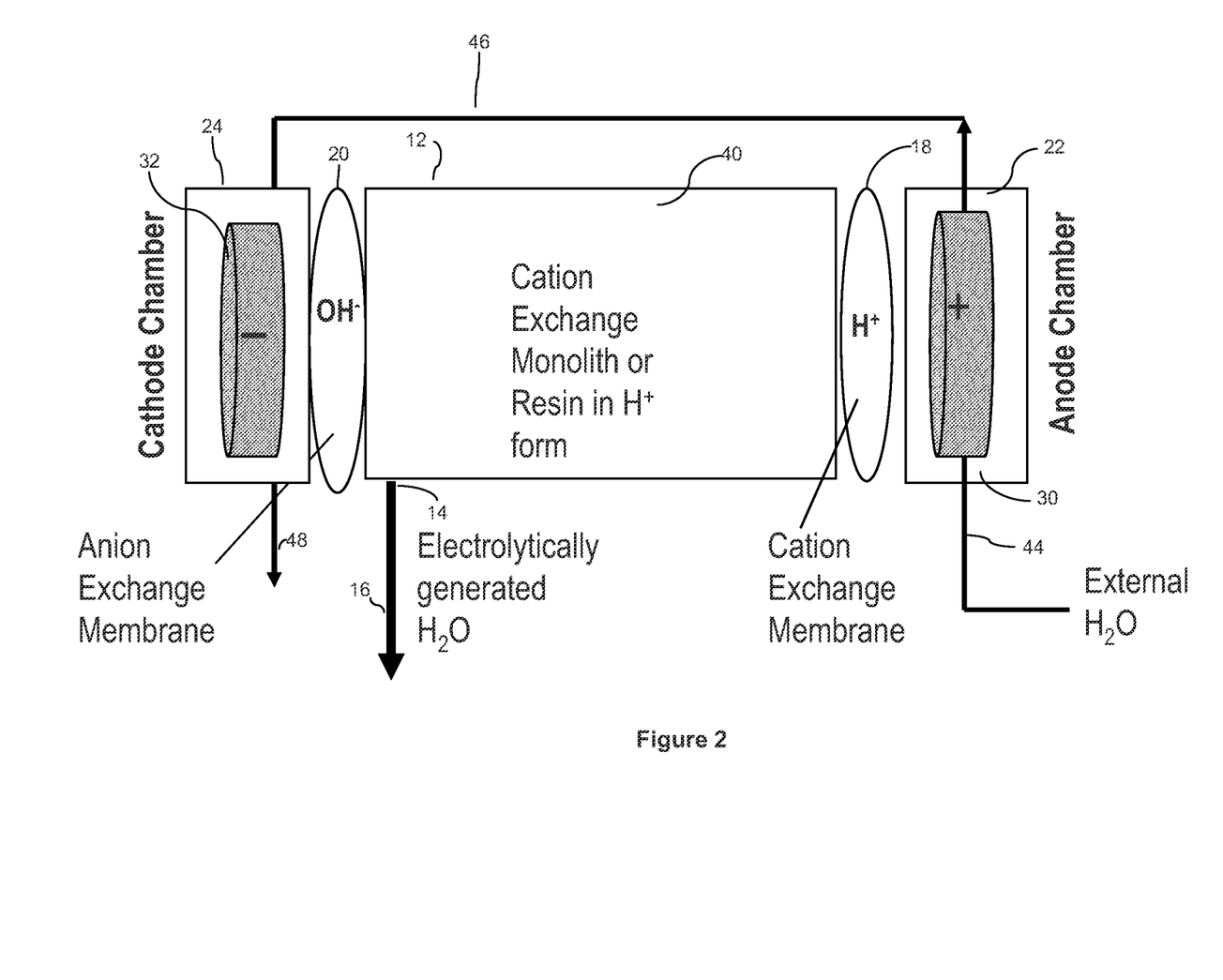

FIG. 2 illustrates an ECP according to the invention fabricated by modifying an Atlas® suppressor of Dionex Corporation, designated "Pump 2" herein. It is in cylindrical cross-section. Like parts with FIG. 1 are labeled with like numbers. The illustrated components are disposed in a cylindrical housing, not shown. Anode chamber 22 includes an anode 30 directly contacting cation-exchange membrane 18. A suitable form of anode 30 is a crumpled conductive metal, e.g. platinum wire. A cation-exchange monolith or ion-exchange resin bed 40 in $H^+$ form is disposed in generation chamber 12 to provide ion transport properties to facilitate movement across the membranes. External water is supplied in line 44 to anode compartment 22 and cycled through line 46 to supply water to both reservoirs. Water exits compartment 44 via line 48. Flow of the source water could be reversed or recycled in the ECP. Also, separate water streams for each compartment or non-flowing reservoirs could be used in compartments 22 and/or 24.

In Pump 2, cation exchange monolith disks may be disposed in the water generation chamber can be prepared similarly according to the process that is described in U.S. Pat. No. 6,610,546 and incorporated herein by reference. The base material for preparation of a cation exchange monolith can be porous polyethylene in sheet or rod form with a preferred porosity of about 35 µm (Porous Technologies). A preferred porosity range for the base material varies from 5 µm-100 µm. The above material can be cut into small pieces in form of disks and is soaked in a solution of 40-60% styrene (preferred range is 20-100% graft level) w/w in methylene chloride solvent. In one embodiment, the sheet material has a preferred thickness of 1.6 mm before grafting. Grafting can be accomplished by irradiation with gamma rays at a dose of 10,000 rads/hour for about 48-120 hours at 80-90° F. under nitrogen atmosphere. The material can then be soaked in 10% w/w chlorosulfonic acid in methylene chloride or suitable solvent for 4 hours at about 40° C. The material can then be immersed in 1M KOH at 55° C. for 30 minutes and then rinsed and washed with DI water.

During operation of Pump 2, like other ECPs, product water flows out line 16 through port 14, the only one open in generation compartment 12. However, a second port, not shown, for compartment 12 can be added, e.g., for ion-exchange conversion of monolith or packed bed 40 to the desired ionic form and for rinsing and rapidly displacing the void volume in compartment 12.

As illustrated, water is pumped to source reservoirs in compartments 22 and 24. A pump, not shown, supplies water to these compartments. One suitable pump is capable of pumping water at a few mls/min, against moderate back pressure (e.g., <50 psi) with fluctuations of up to 10% in flow rate. A simple peristaltic pump can be used, However, a higher performance pump such as the Dionex GP 40 gradient pump may be used for specific applications.

An adjustable current source, e.g. a Keithley 220 Programmable Current Source, can be used to supply the current to the ECP during operation. This component is omitted from FIGS. 1 and 2.

Figure 3A:
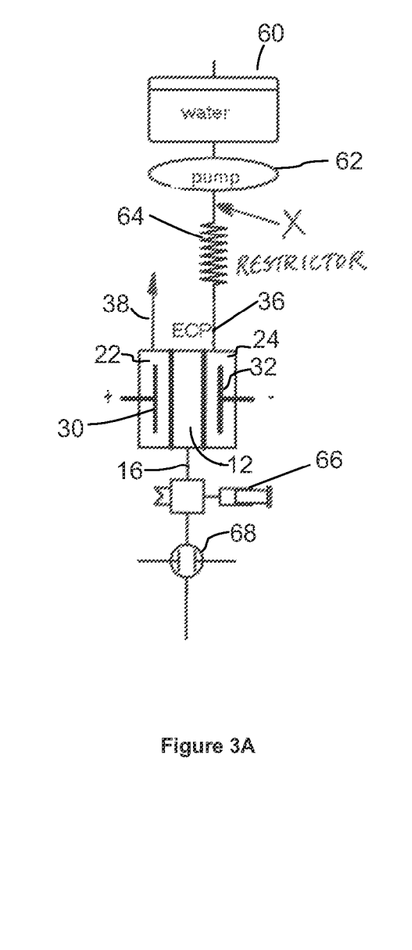
Figure 3B:
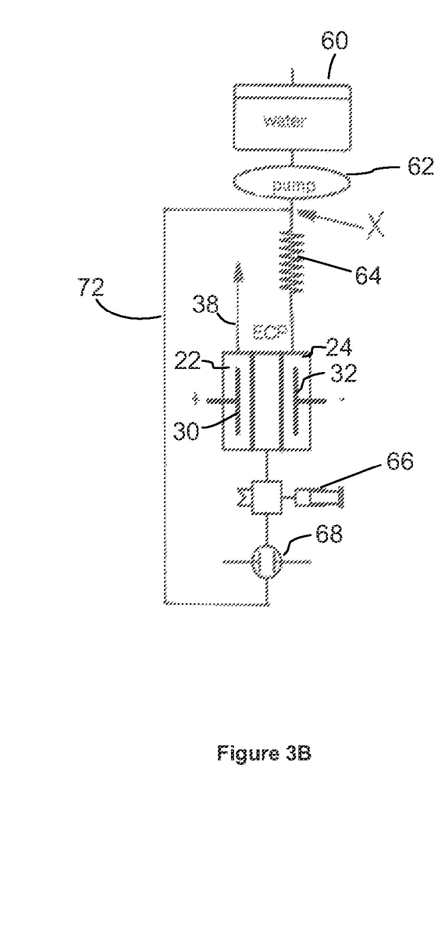

Referring to FIGS. 3A and 3B, test systems are illustrated using the ECP of FIG. 1. Like parts will be designated with like numbers. Water from reservoir 60 is pumped by pump 62 through flow restrictor 64 in line 36 to compartment 24 and from there to compartment 22 and out line 38. The product stream in line 16 flows through sample injector 66 and to detector 68 (e.g. a conductivity detector). FIG. 3B differs from FIG. 3A by the inclusion of a recycle line 72 from detector 68 to provide some of the water to compartment 24. If desired, a small de-ionizing device, not shown, may be placed in line 16 or in recycle line 72. (For LC a chromatography column (not shown) is disposed between injector 66 and detector 68. For suppressed IC, a suppressor (not shown) is additionally disposed between the chromatography column and detector 68.)

An advantage of Pump 2 over Pump 1 is that Pump 2 is capable of operating better at higher pressures.

Figure 4:
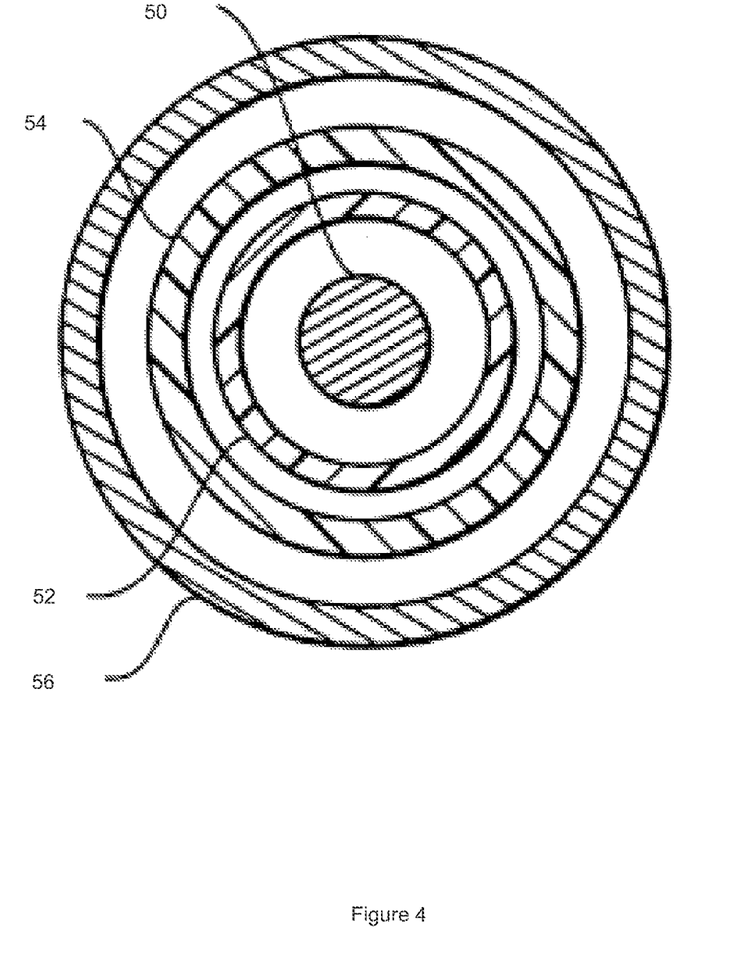

Another embodiment of the ECP is formed of substantially concentric tubes with structure similar to the an electrolytic suppressor in FIG. 8 of the '360 patent. As illustrated in FIG. 4 herein, the concentric tube ECP is generally constructed by inserting a length of suitable inert conductive metal wire as an inner electrode 50 into a length of tubular inner ion exchange membrane 52 which is itself inserted inside a length of somewhat larger diameter tubular outer ion exchange membrane 54. The whole assembly is enclosed in a conductive metal (e.g. stainless steel) tube 56 of appropriate dimensions. The outer tube 56 itself functions as an electrode, connections being made at the ends to allow access to the flow channels between the inner electrode and inner membrane, in the space between the two membranes (annulus) and between the outer membrane and stainless steel case. Inner transport bridging structure of the foregoing type can be inserted into one or more of the flow channels between the concentric tubes.

In another embodiment, not shown, the ECP of the present invention (e.g. in the embodiments of FIGS. 1, 2, 3A, 3B and 4) can be used as a concentrator for detecting anionic and/or cationic impurities in a water sample. Any of the ECP embodiments described herein can be used as the concentrator. In this system, the water in the anode and cathode compartments comprises reservoirs of two portions of a water sample. The cationic and anionic impurities in the water sample are the analytes to be detected. Here, the detector is in fluid communication with the water generator compartment outlet. Since the analyte-containing water sample is in the anode and cathode compartments, there is no sample injector disposed between the water generator compartment outlet and the detector.

In operation of the concentrator, the water sample is split into the reservoirs of water in the anode and cathode compartments. The hydroxide ions electrolytically generated in the water sample in the cathode compartment and anionic analytes in that compartment pass through the ion exchange barrier into the water in the generator compartment. The hydronium ions electrolytically generated in the water sample in the anode compartment and analytes in that compartment pass through the cationic exchange barrier into water in the generator compartment in which water is generated as set forth above. The generated water sample containing the contaminant cation and anion analytes flows to a detector. No additional sample is injected between the generator compartment and the detector. In one embodiment, the cation exchange hairier includes exchangeable ions predominantly in the hydronium ion form and the anion exchange barrier includes exchangeable ions predominantly in the hydroxide form.

An illustration of how the ECP can be used as a concentrator is as follows. Assume that, in the water stream of interest, the concentration of the impurity electrolytes is 'c units/ml'. For the purpose of this illustration it is not necessary to state the units used to describe 'c'. Assume that the water stream is applied to the electrode compartments of the ECP at a flow rate of 'V' mls/minute. Therefore the amount of impurity passing through the electrode compartments is 'Vc' units/minute.

While the electrode compartments are being flushed with the water stream of interest, current is applied to the ECP thus producing flow from the middle compartment. Assume the flow rate from the ECP is represented as 'p' mls/minute. In typical operation of an ECP, 'V' is very much larger than 'p'. Assume that V/p equals 1000 [a reasonable figure given that 'V' might be 1 ml/min while 'p' is 1 microliter/min].

Because the concentration of analyte ions in the water supplied to the ECP is very low, the preponderance of ions crossing the membranes into the central compartment will be hydronium and hydroxide. But the impressed current will also carry impurity ions into the central compartment. It would be ideal if all of the analyte ions could be captured and transferred to the central compartment. However, assuming that only 10% of the analyte is captured and the rest escapes, the amount transferred to the central compartment is 10% of 'Vc' or 0.1 Vc units/minute. Assuming that the flow from the ECP is 'p' and further that p=V/1000, it follows (from mass balance) that 0.1 Vc (the amount entering the central compartment) must equal the amount leaving which is 'pC' where 'C' is the concentration of the analyte in the solution leaving the central compartment.

Thus 0.1 Vc=pC

Or 0.1 Vc=(V/1000)C

Therefore C=100 c

Based on these assumptions, a hundred-fold concentration of the analyte is achieved. This concentrated analyte stream could he detected by a conductivity cell thus enhancing detectability or it could be passed to the sample loop of an injector in an ion chromatographic system.

In another embodiment, not shown, the ECP of the present invention cart be used in combination with a flow controller in fluid communication with the outlet conduit from the ECP water generation compartment. In one embodiment, the flow controller includes a feedback circuit. For example, a flow sensor can measure the flow rate of water in the ECP outlet conduit is measured, and appropriate control electronics can provide feedback to the constant current source to adjust the applied current so that the ECP pump provides a controllable and constant output flow rate. This is useful, for example, if membrane permeation provides a significant flow from the anode and cathode compartments to the generator compartment.

In order to illustrate the present invention, the following non-limiting examples of its practice are required.

Example 1

This example uses a Pump 1 embodiment of ECP.

The ECP Pump 1 was constructed using components similar to those used in Dionex SRS suppressors. The general construction of Dionex SRS suppressors is similar to the embodiment of the electrolytic suppressor described in FIG. 2 of U.S. Pat. No. 5,352,360. Parameters relevant to the components and their functions are set out in U.S. Pat. No. 5,352,360 and are incorporated herein by reference.

In the ECP Pump 1 shown in FIG. 1, the anion SRS suppressor (ASRS) chromatography effluent channel was used as the central water generator compartment 12 by plugging its inlet port. The water generator compartment was partially bounded by the chromatography effluent gasket defining a central cavity. A flow-through sulfonated cation exchange screen was disposed in the cavity. Two ion exchange membrane sheets were mounted to extend along opposite sides of central water generator compartment and defined the outer perimeter of the central water generator compartment together with gasket. The ASRS anode regenerant channel was used as the ECP anode compartment 22 without modification. The ECP cathode compartment 24 was prepared by modifying the ASRS cathode regenerant channel. Both sulfonated cation exchange membrane and screen in the ASRS cathode regenerant channel were replaced with aminated anion exchange membrane and screen. The fluidic inlet and outlet ports ECP anode and cathode compartments were constructed in the same manner as the inlet and outlet ports of the ASRS anode and cathode regenerant channels.

Referring to FIG. 3A, pump 62 was a Dionex GP 40. The reservoirs in compartments 22 and 24 contained de-ionized water. The water from the GP 40 passed through a deionizer, (a small bed of mixed resin (not shown)) that reduced the conductivity of the water to about 130 nanosiemens.

The water then flowed through a flow restrictor 63 (several meters of PEEK tubing, 0.005 inches ID) which at moderate flow rates raised the pressure at point X to significantly high levels (600 to 1200 psi, depending on the flow rate).

The water from the restrictor 63 was then directed through the compartments 22 and 24 and exited to waste along with the electrolysis gases.

The output conduit 17 of the ECP connected the ECP to a conventional IC injection valve 66 equipped with a sample loop of 25 micro liters nominal volume, The pathway beyond the conductivity cell depended on the objective.

If the objective was to measure the flow rate of the ECP while it was discharging to atmosphere then the configuration of FIG. 3A was used.

But if the objective was measuring flow rate against backpressure, then the exit of the conductivity cell 66 was connected back to the system in recycle line 72 at point-X by way of a T-piece (FIG. 3B). In this configuration, the ECP pumps against whatever backpressure is generated at point-X. Furthermore, this backpressure must be maintained at a constant level during a flow measurement, using the Dionex GP 40. Its stability and precision of flow combined with its ability to maintain this flow against significant backpressure were reasons for choosing it over a simpler type of pump.

Using this configuration the ECP pumping rate was measured at three different backpressures: 638, 950 and 1223 psi., generated by flow rates from the GP 40 of 0.2, 0.3 and 0.4 ml/min. respectively.

Measuring the Output of the ECP

Two methods were employed for determining the pumping rate of the ECP

Method 1. Total displacement of the contents of the sample-loop.

This method measured the time necessary to drive the complete contents (0.01M KCl) of the sample loop through the conductivity cell.

Figure 5:
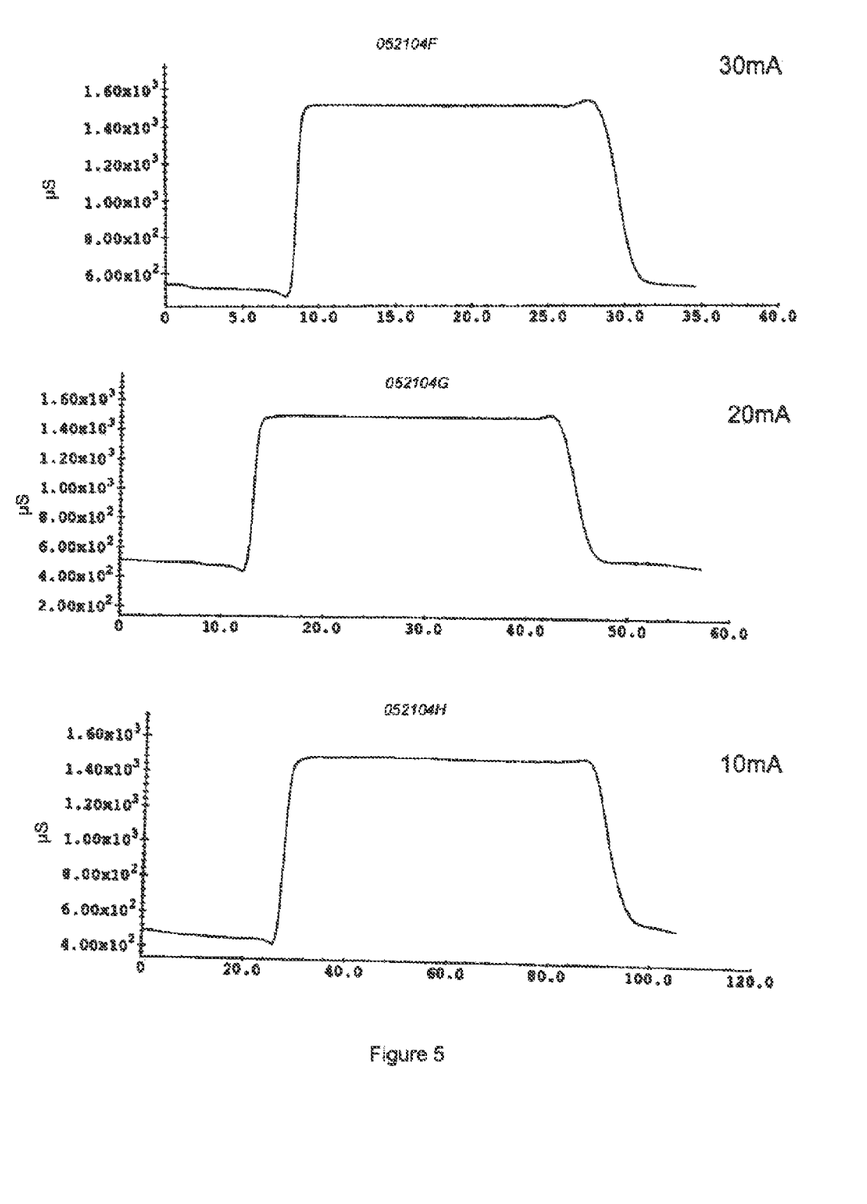
FIGS. 5-8 are graphical representations of experimental results using the above apparatus and method according to the present invention.

A measurement consisted of switching the sample loop into the system and leaving it there until the contents of the loop had passed through the conductivity cell and the conductance of the ECP effluent had returned to its initial level (FIG. 5 below).

FIG. 5 illustrates the displacement of the sample-loop contents by the ECP operating at three different currents; 10, 20 and 30 milliamps. The sample-loop (nominal volume 25 μL) was determined (experimentally) to be 27 μL. The flow rate, in μL/minute, was determined by dividing this volume by the expulsion-time-interval of the loop contents. This time was the difference between two times; the time halfway up the rising arm of the conductivity wave and the time halfway down the falling arm of the conductivity wave.

Method 2. Transit Time of a Short Sample Pulse

In this method the sample loop was switched briefly into the system (for 0.1 minute) and then removed again. At typical flow rates of the ECP it takes a few minutes for this short pulse of electrolyte to reach the conductivity cell. We call this delay the "transit time" of the pulse and again the software of the system allowed us to make a precise measurement of the transit time of this small pulse of KCl between the sample valve and the conductivity cell. By combining such a measurement with a measurement by the first method we had a means of accurately translating these transit times into flow rates. Most of the flow rates reported here were determined by the Method 2.

Method 3. The Weighing Method

The most accurate method for determining flow rate is by weighing the product from the ECP. It is however a very slow method requiring several hours of collection to accumulate an amount of water that can be weighed with adequate accuracy. It is therefore unsuitable for "on-the-fly" measurements of flow rate from an ECP. When combined with the transit-time measurements the weighing method provides a means for accurately calibrating the transit-time method.

Example 2

Examples of the ECP in Operation

Pump 1: Flow rate versus current at atmospheric pressure.

Table 1 summarizes the results of measuring the flow rate of Pump 1 at six different currents with the pump discharging to atmosphere.

The second column lists the measured flow rates while the third column gives the faradaic flow rates (see "The Pumping Mechanism") calculated for each current. By dividing the measured flow rate by the faradaic flow rate one obtains a figure for the total number of moles of water (faradaic plus hydration plus electroosmotic) transported per faraday (column 4)

TABLE 1

| Current mA | Measured Flow Rate μL/min | Faradaic Flow Rate, μL/min | Measured Flow Rate/Faradaic Flow Rate |
|---|---|---|---|
| 10 | 0.423 | 0.112 | 3.78 |
| 20 | 0.856 | 0.224 | 3.82 |
| 30 | 1.28 | 0.336 | 3.81 |
| 40 | 1.72 | 0.448 | 3.84 |
| 50 | 2.16 | 0.56 | 3.85 |
| 60 | 2.63 | 0.672 | 3.91 |

Figure 6:
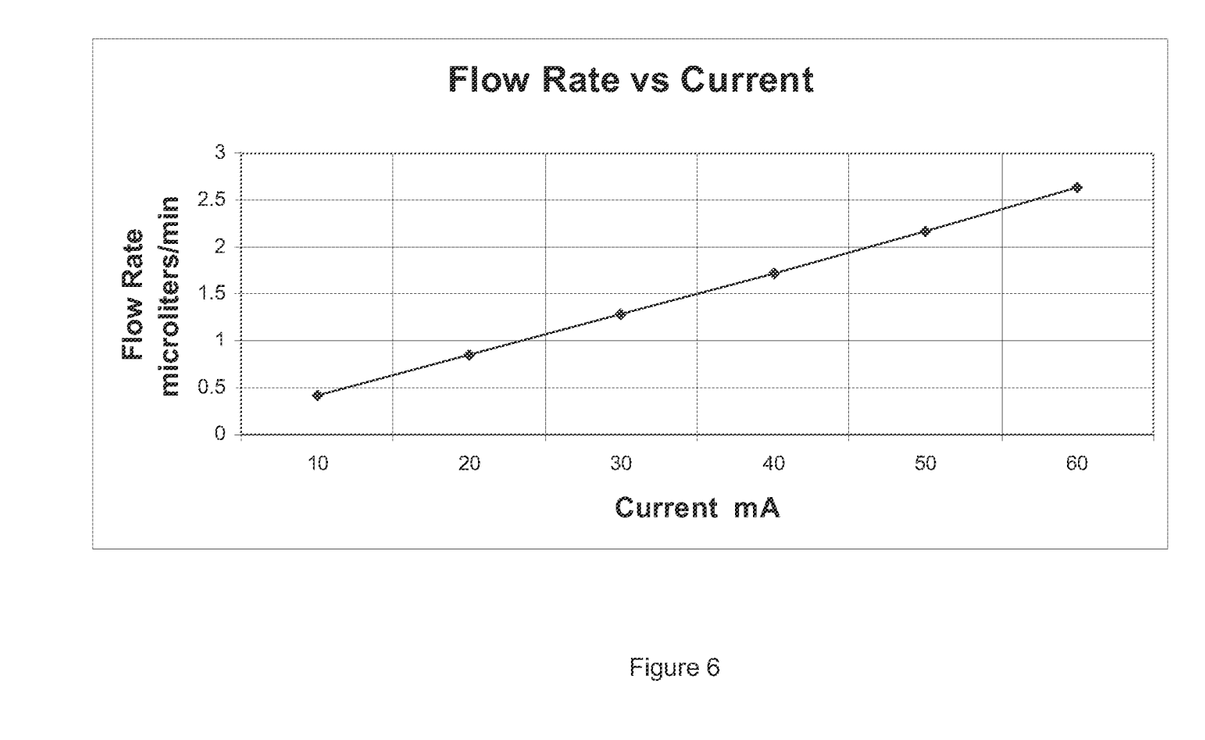

FIG. 6 shows the linear dependence of flow rate on applied current and suggests a simple method for controlling the output of the ECP.

Pump 2: Flow rate versus current and applied backpressure.

The ECP Pump 2 was constructed using components similar to those used in Dionex anion Atlas electrolytic suppressors (AAES). The general construction of Dionex anion Atlas electrolytic suppressors is similar to the embodiment of the electrolytic suppressor described in FIG. 6 of U.S. Pat. No. 6,610,546. Parameters relevant to the components and their functions are set out in U.S. Pat. No. 6,610,546 and are incorporated herein by reference.

In the ECP Pump 2 shown in FIG. 2, the central water generator compartment 12 was a cylindrical cavity (6 mm in diameter and 10 mm in length) with an inlet port and an outlet port. The inlet port is plugged when the device is used as an electrochemical pump. The cavity was packed with six sulfonated cation exchange monolith disks (6 mm in diameter and 0.16 mm in thickness). The AAES anode regenerant chamber was used as the ECP anode compartment 22 without modification. The ECP cathode compartment 24 was prepared by modifying the AAES cathode regenerant chamber. Both sulfonated cation exchange membranes and monolith disk in the AAES cathode regenerant chamber were replaced with aminated anion exchange membranes and monolith disk. The inlet and outlet ports of the AAES anode and cathode regenerant chambers were used as the fluidic inlet and outlet ports ECP anode and cathode compartments.

One of the first tests of Pump 2 illustrated in FIG. 2 herein examined its stability over several hours of running, at 40 mA current and discharging to atmosphere.

Table 2 shows the results of that test. The pump displays very stable flow over this sort of time interval and is typical of the tested pumps

TABLE 2

| Time of day | Transit time (min) |
|---|---|
| 12:47 pm | 7.22 |
| 12:57 pm | 7.23 |
| 1:07 pm | 7.23 |
| 2:48 pm | 7.17 |
| 4:20 pm | 7.15 |
| 5:34 pm | 7.12 |
| 6:40 pm | 7.12 |
| 7:46 pm | 7.13 |
| 9:46 pm | 7.12 |

(A transit time of 7.13 minutes translates to a flow rate of 1.55 μL/min.)

Table 3 summarizes the results of flow measurements made on pump 2 running at five different currents and against zero (atmospheric), 638, 950 and 1223 psi backpressure. Column 3 lists the flow rates measured at the various currents and backpressures. Column 4 lists a quantity that we have called membrane permeation. The description of membrane permeation is as follows.

All membranes, especially those containing water of hydration, can be expected to allow hydraulic "leakage" of water when water under pressure is forced against them; the technology known as reverse osmosis relies on this property. Consequently, when an ECP is pumping against backpressure we can expect some backflow of water through the membranes. We have called this type of flow membrane leakage or membrane permeation. This is flow subtracted from the electrochemical pumping. An objective of this set of experiments was to measure membrane permeation.

Membrane permeation at a particular current and backpressure is calculated in the following way.

It is assumed that when the ECP is pumping to atmospheric pressure that the membrane permeation is zero and therefore the first five flow rates listed in Table 3 represent the electrochemically-produced flow rates at the various currents.

Taking the measurement at 30 mA and 638 psi backpressure as an example, the flow rate is 1.06 μL/minute. This is 0.11 μL/minute less than the flow rate measured at 30 mA and zero backpressure. This difference can be attributed to membrane permeation. All the values listed in column 4 were calculated in this way.

TABLE 3

| Backpressure (psi) | Current (mA) | Flow rate (μL/min) | Membrane permeation (μL/min) |
|---|---|---|---|
| 0 | 10 | 0.42 | — |
| 0 | 20 | 0.80 | — |
| 0 | 30 | 1.17 | — |
| 0 | 40 | 1.57 | — |
| 0 | 60 | 2.36 | — |
| 638 | 10 | 0.27 | 0.15 |
| 638 | 20 | 0.67 | 0.13 |
| 638 | 30 | 1.06 | 0.11 |
| 638 | 40 | 1.43 | 0.14 |
| 638 | 60 | 2.21 | 0.15 |
| 950 | 10 | 0.19 | 0.23 |
| 950 | 20 | 0.57 | 0.23 |
| 950 | 30 | 0.95 | 0.22 |
| 950 | 40 | 1.33 | 0.24 |
| 950 | 60 | 2.09 | 0.27 |
| 1223 | 10 | 0.15 | 0.27 |
| 1223 | 20 | 0.52 | 0.28 |
| 1223 | 30 | 0.90 | 0.27 |
| 1223 | 40 | 1.29 | 0.28 |
| 1223 | 60 | 2.08 | 0.28 |

Figure 7:
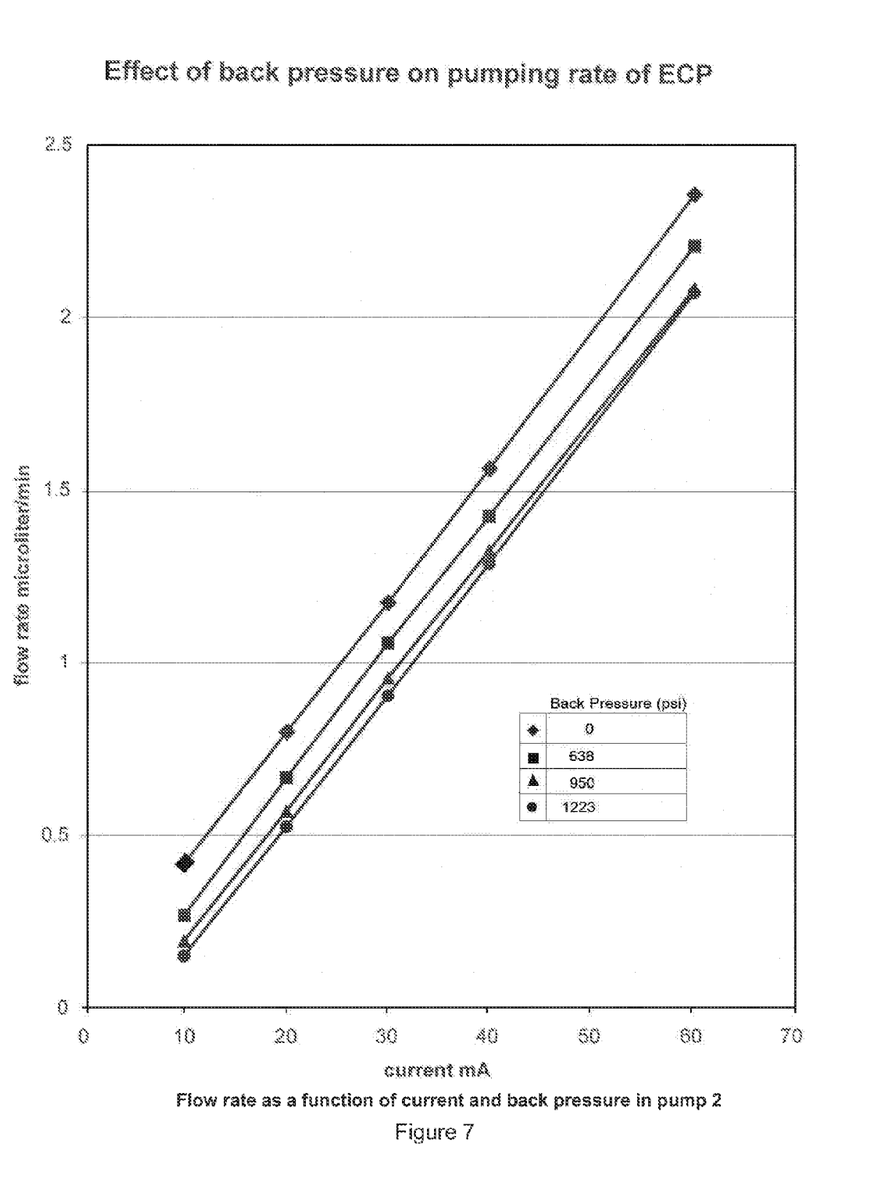

Although membrane permeation can be a significant flow, the ECP still can be useful as a commercial device, particularly since permeation may be reduced by changes to membrane structure and thickness. Furthermore, the simple dependence of flow rate on current, regardless of backpressure (FIG. 7) is encouraging. It should be pointed out that the loss of water through the membrane leakage can be compensated by using a flow sensor to measure the flow and using appropriate control electronics to provide feedback to the constant current source to adjust the applied current so that the ECP pump provides a controllable and constant output flow rate. One flow sensor is ASL1600 media isolated liquid mass flow meter manufactured by SENSIRION AG (Zurich, Switzerland). The flow meters and controllers of the types described in U.S. Pat. Nos. 4,532,811 and 6,813,944 may also be used.

Table 4 lists the raw data from the measurements of transit times measured at the highest backpressure, 1223 psi. We include these actual transit times, run in duplicate, to show the remarkable stability of flow rate of the ECP.

At the lowest current were the transit time is about 74 minutes, and the two measurements were made at least 74 minutes apart, the agreement between duplicate measurements is indeed remarkable.

TABLE 4

| Current (mA) | Transit time (min) |
|---|---|
| 60 | 5.30 |
| 60 | 5.30 |
| 40 | 8.55 |
| 40 | 8.55 |
| 30 | 12.20 |
| 30 | 12.22 |
| 20 | 21.02 |
| 20 | 21.02 |
| 10 | 73.67 |
| 10 | 73.68 |

Pump 3: Flow rate versus current and backpressure.

Pump 3 is the same as Pump 2 but with a shorter (5 mm long) compartment B to allow higher currents of operation than Pump 2.

Figure 8:
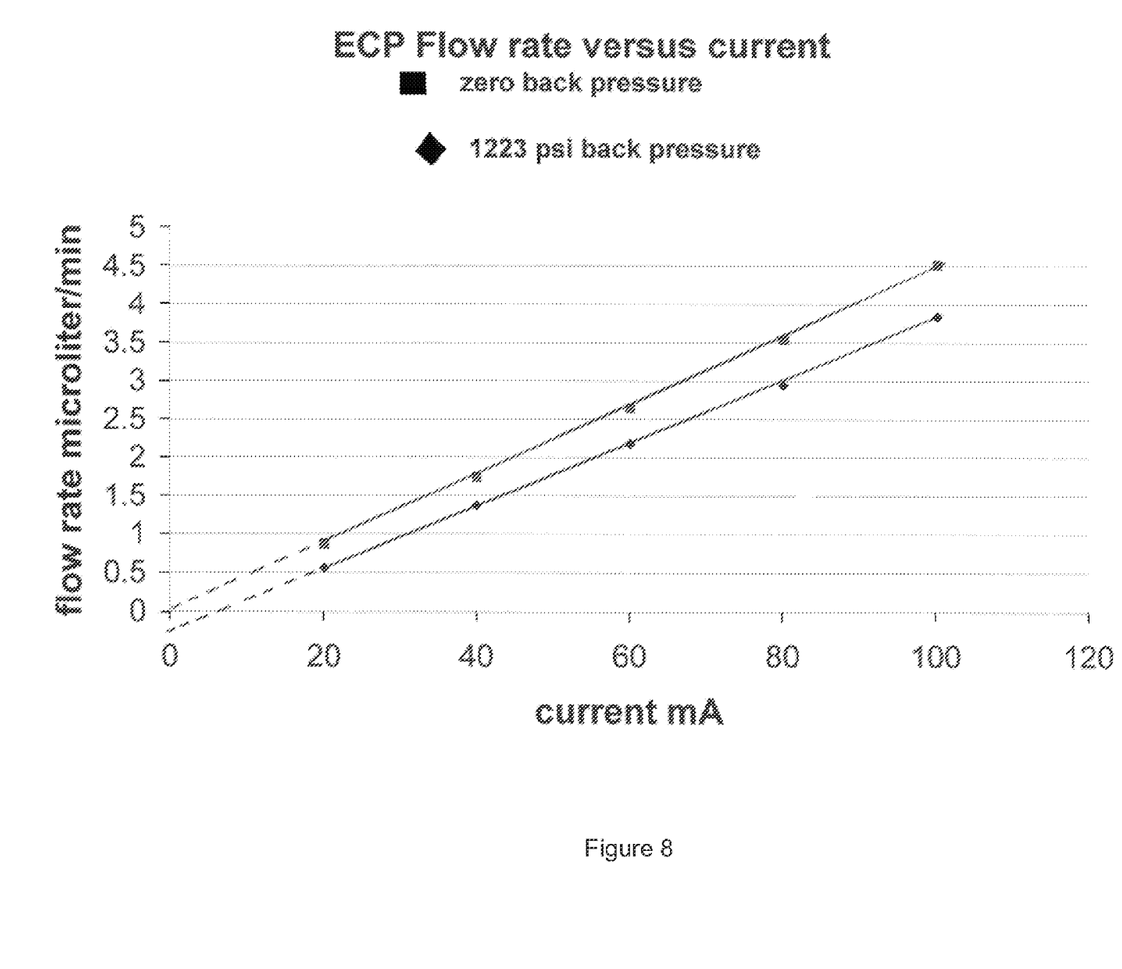

Tables 5 and 6 and FIG. 8 give the results of flow measurements at zero and 1223 psi backpressure respectively. The raw data for triplicate measurements of transit times (column 3) are included to show the stability of flow that is typical of these ECPs. The voltages applied to the ECP at the various currents are listed in column 2.

TABLE 5

Pump 3 pumping to atmosphere

| Current (mA) | Voltage (volts) | Transit Time (minutes) | Flow Rate (µL/min) | Membrane Permeation (µL/min) |
|---|---|---|---|---|
| 100 | 15.0 | 2.45 | 4.51 | zero |
|  |  | 2.45 |  |  |
|  |  | 2.43 |  |  |
|  |  | ave. 2.443 |  |  |
| 80 | not available | 3.12 | 3.53 | zero |
|  |  | 3.12 |  |  |
|  |  | 3.12 |  |  |
|  |  | ave. 3.12 |  |  |
| 60 | 12.7 | 4.17 | 2.64 | zero |
|  |  | 4.17 |  |  |
|  |  | 4.17 |  |  |
|  |  | ave. 4.17 |  |  |
| 40 | 10.7 | 6.35 | 1.74 | zero |
|  |  | 6.33 |  |  |
|  |  | 6.35 |  |  |
|  |  | ave. 6.337 |  |  |
| 20 | 7.6 | 12.63 | 0.873 | zero |
|  |  | 12.63 |  |  |
|  |  | 12.62 |  |  |
|  |  | ave. 12.63 |  |  |

TABLE 6

Pump 3 pumping against 1223 psi backpressure

| Current (mA) | Voltage (volt) | Transit Time (min) | Flow Rate (µL/min) | Membrane Permeation (µL/min) |
|---|---|---|---|---|
| 100 | 16.0 | 2.88 | 3.84 | 0.67 |
|  |  | 2.87 |  |  |
|  |  | 2.87 |  |  |
|  |  | ave. 2.873 |  |  |
| 80 | 14.9 | 3.75 | 2.94 | 0.59 |
|  |  | 3.75 |  |  |
|  |  | 3.75 |  |  |
|  |  | ave. 3.75 |  |  |
| 60 | 13.9 | 5.05 | 2.18 | 0.46 |
|  |  | 5.07 |  |  |
|  |  | 5.03 |  |  |
|  |  | ave. 5.05 |  |  |
| 40 | 11.9 | 8.03 | 1.37 | 0.37 |
|  |  | 8.03 |  |  |
|  |  | 8.03 |  |  |
|  |  | ave. 8.03 |  |  |
| 20 | 8.6 | 19.70 | 0.56 | 0.31 |
|  |  | 19.70 |  |  |
|  |  | ave. 19.70 |  |  |

In Pump 3, the membrane permeation is higher than in pump 2 and that it increases with current; membrane permeation in pump 2 was apparently independent of current. It is believed that this behavior can be explained as follows.

In Pump 3, the volume of compartment 22 is about 50% of that in Pump 2 so any electrical heating is being impressed on a smaller volume and we would expect it to cause more heating of the contents of compartment 22. Furthermore, we would expect the heating effect to rise with increasing current. This increase in temperature in compartment 22 will lead to higher membrane temperature thus reducing the viscous drag on water as pressure forces it through the membrane. This could explain why the membrane permeation is higher than in pump 2 and why it rises with current.

Conclusions Regarding The Quality Of The Water Produced By The Ecp

The description of the invention implies that the ECP pumps pure water. In practice, the product of the ECP pumps may have a conductance of several hundred microsiemens. There are a number of theoretical reasons for this. In the first place, if the membranes are not completely in their hydronium and hydroxide forms then contaminating cations and anions can be electrochemically driven into the fluid in compartment 22 thus raising its conductance. Considering the relatively minute flows from compartment B, a small flux of contaminating ions could easily raise the conductance of the ECP product to the levels that we observe. In a device such as Pump 1, where the total area of the membrane is exposed to the electrochemical ion flux, continued operation of the ECP should quickly remove the contaminating ions. However, in pumps like Pump 2 and Pump 3 where a considerable area of the ion-exchange membranes in the anode and cathode chambers is shielded (by clamping) from the electrical field, removal of ions from the shielded volume will he diffusion controlled and relatively slow. So if membranes are not in their ideal form initially, poor quality water product may persist for some time. If the ion-exchange material in compartment 22 has a tendency to leach polymeric fragments this also may be a source of added conductance.

There is also a fundamental reason for expecting that the water produced from the ECP can never be pure. It is not feasible to produce absolutely pure water for flushing the electrode compartments 22 and 24; this water will always contain some level of contaminating ions. These ions will be carried with the hydronium and hydroxide ions into compartment 22 and raise its conductivity.

Assuming the foregoing contaminants, there are remedies that can make the ECP an acceptable water pump as described briefly above. As discussed above, the first is simply to add a small de-ionizing column (or other de-ionizing device) to the outlet of the ECP. If membranes and electrode-flushing water are prepared in relatively pure form then the load on such a polishing bed can be relatively low and it will last a long time before it needs to be replaced.

Advantages of the ECP method and pump include the following:

(1) It is compact.
(2) It is easily fabricated.
(3) It has no motors, check valves, pistons or other moving parts to limit its durability.
(4) Its flow is easily and precisely controlled.
(5) It can pump against considerable backpressure.
(6) By a simple modification (e.g. the liquid piston), it can pump any fluid in a controlled way.
(7) It can have a wide range of application when controlled low flow rate of liquids is the objective.

What is claimed is:

1. A continuous electrochemical concentrator in an analytical system comprising:
  (a) a water generator compartment having an outlet,
  (b) an anode compartment disposed adjacent one side of said generator compartment,
  (c) a cation exchange barrier separating said generator compartment from said anode compartment, said cation exchange barrier being capable of passing cations but not anions and of blocking bulk liquid flow,
  (d) a first electrode in electrical communication with said anode compartment,
  (e) a cathode compartment disposed adjacent said generator chamber,
  (f) an anion exchange barrier separating said generation compartment from said cathode compartment, said anion exchange barrier being capable of passing anions but not cations and of blocking bulk liquid flow,
  (g) a second electrode in electrical communication with said cathode compartment, and
  (h) a detector in fluid communication with said water generator compartment outlet in the absence of a sample injector for the supply of sample, other than sample supplied from said water generator compartment outlet, disposed between said generator compartment outlet and said detector.

2. The concentrator of claim 1 further comprising reservoirs of sample water in said anode and cathode compartments.

3. A method for concentrating and detecting analyte anions and cations in a water sample using a concentrator comprising an aqueous liquid generator compartment having an outlet; an anode compartment containing a first portion of said analyte anion- and cation-containing water sample and disposed adjacent to said generator compartment; a cation exchange barrier separating said generator compartment from said anode compartment; said cation exchange barrier being capable of passing cations but not anions and of blocking bulk liquid flow, a first electrode in electrical communication with said anode compartment; a cathode compartment containing a second portion of said analyte anion- and cation-containing water sample and adjacent to said generator chamber; an anion exchange barrier separating said generator compartment from said cathode compartment; said anion exchange barrier being capable of passing anions but not cations and of blocking bulk liquid flow, and a second electrode in electrical communication with said cathode compartment, said method comprising:
  (a) passing an electric current between said first and second electrodes through said first and second water sample portions in said anode and cathode compartments, and through said cation and anion exchange membranes, to generate hydroxide ions in said cathode compartment and hydronium ions in said anode compartment,
  (b) passing said generated hydroxide ions and analyte anions in said water sample through said anion exchange barrier and said generated hydronium ions and analyte cation in said water sample through said cation exchange barrier into said generator compartment to electrochemically generate a water product sample including said passed analyte cations and anions, and
  (c) flowing said generated water product sample in a stream out of said generator compartment to a detector to detect said analyte cations and anions in said water product sample in the absence of the injection of any additional sample between said generator compartment and said detector.

4. The method of claim 3 in which the cation exchange barrier includes exchangeable ions predominantly in the hydronium ion form and the anion exchange barrier includes exchangeable ions predominantly in the hydroxide ion form.

* * * * *